(12) United States Patent
Salcudean et al.

(10) Patent No.: US 9,801,615 B2
(45) Date of Patent: Oct. 31, 2017

(54) QUANTITATIVE ELASTOGRAPHY WITH TRACKED 2D ULTRASOUND TRANSDUCERS

(71) Applicant: The University of British Columbia, Vancouver (CA)

(72) Inventors: Septimiu Edmund Salcudean, Vancouver (CA); Caitlin Marie Schneider, Vancouver (CA); Robert N. Rohling, Vancouver (CA); Ali Baghani, Vancouver (CA)

(73) Assignee: The University of British Columbia, Vancouver (CA)

( * ) Notice: Subject to any disclaimer, the term of this patent is extended or adjusted under 35 U.S.C. 154(b) by 46 days.

(21) Appl. No.: 14/040,558

(22) Filed: Sep. 27, 2013

(65) Prior Publication Data

US 2017/0020486 A1    Jan. 26, 2017

Related U.S. Application Data

(60) Provisional application No. 61/707,883, filed on Sep. 28, 2012.

(51) Int. Cl.
*A61B 8/08* (2006.01)
*A61B 8/00* (2006.01)
*A61B 8/12* (2006.01)

(52) U.S. Cl.
CPC ............ *A61B 8/485* (2013.01); *A61B 8/4263* (2013.01); *A61B 8/12* (2013.01)

(58) Field of Classification Search
CPC .......... A61B 8/485; A61B 8/12; A61B 8/4263
See application file for complete search history.

(56) References Cited

U.S. PATENT DOCUMENTS

| | | | | |
|---|---|---|---|---|
| 5,538,004 A | * | 7/1996 | Bamber | G01S 7/52044 128/916 |
| 2003/0220556 A1 | * | 11/2003 | Porat | A61B 5/0051 600/407 |
| 2005/0252295 A1 | * | 11/2005 | Fink | A61B 8/08 73/603 |

\* cited by examiner

*Primary Examiner* — Bo J Peng
(74) *Attorney, Agent, or Firm* — Oyen Wiggs Green & Mutala LLP

(57) ABSTRACT

A method is described for acquiring 3D quantitative ultrasound elastography volumes. In one embodiment, the method comprises using a 2D ultrasound transducer to scan a volume of tissue through which shear waves are created using an external vibration source, the synchronized measurement of tissue motion within the plane of the ultrasound transducer with the measurement of the transducer location in space, the reconstruction of tissue displacements in time and space over a volume from this synchronized measurement, and the computation of one or several mechanical properties of tissue from this volumetric measurement of displacements. The tissue motion in the plane of the transducer may be measured at a high effective frame rate in the axial direction of the transducer, or in the axial and lateral directions of the transducer. The tissue displacements over the measured volume may be interpolated over a regular grid in order to make the computation of mechanical properties easier.

18 Claims, 7 Drawing Sheets

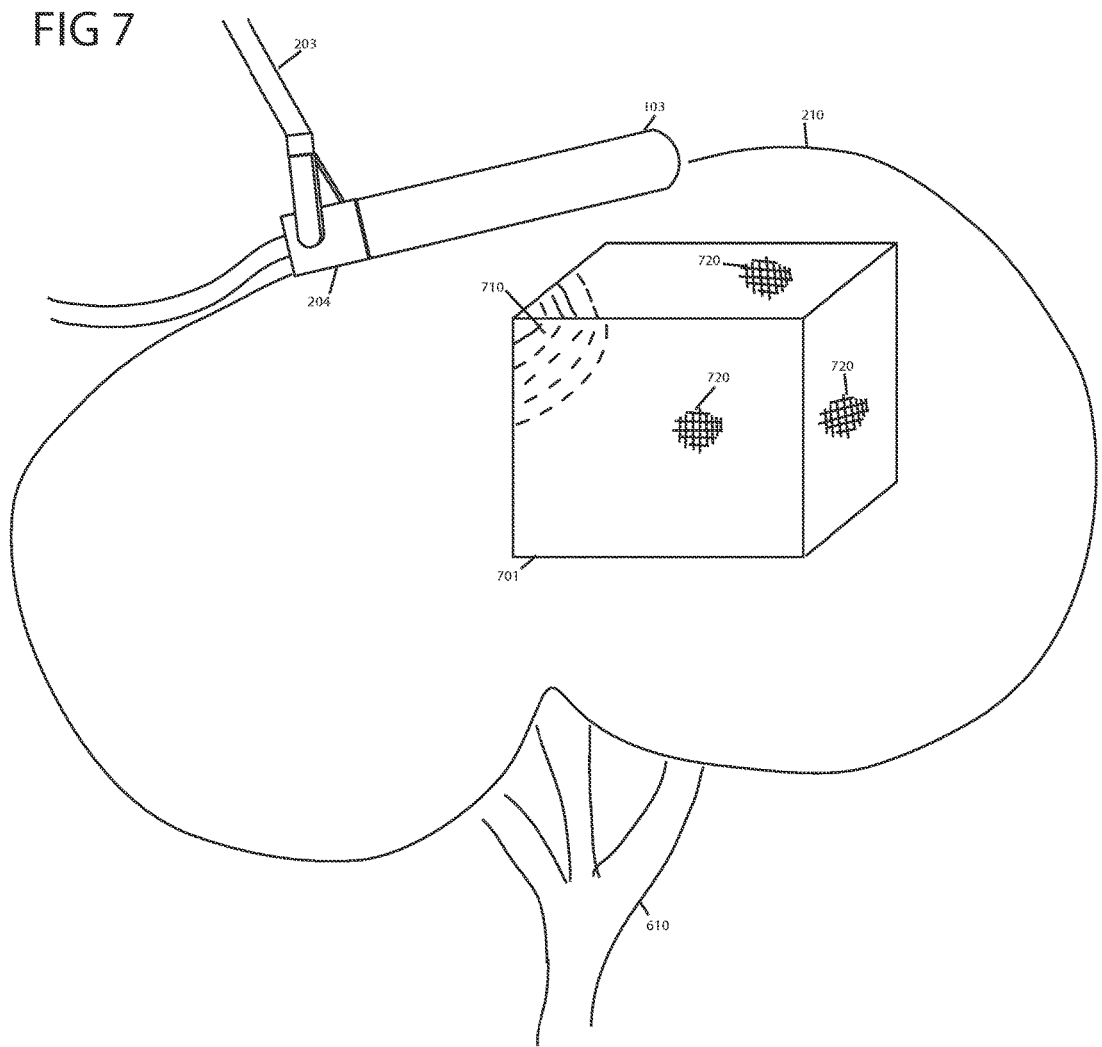

QUANTITATIVE ELASTOGRAPHY WITH TRACKED 2D ULTRASOUND TRANSDUCERS

This application claims priority under 35 U.S.C. §119(e) to a U.S. provisional application having Ser. No. 61/707,883, filed Sep. 28, 2012, the entirety of which is herein incorporated by reference.

FIELD OF THE INVENTION

This invention relates to medical imaging and, in particular, the measurement of mechanical properties of the tissues, also known as elastography.

BACKGROUND OF THE INVENTION

Medical imaging is used in many applications to determine the composition of tissue not visible to the naked eye. The images can be displayed to a user, where the intensity or color of the image is a function of some parameter of the tissue composition. For example, computed tomography (CT) displays to the user the absorption of X-rays in the body and ultrasound displays the echo pattern produced in response to a pulsed sound wave. Of particular interest are the mechanical properties of tissue which can also be depicted in images. Changes in the mechanical properties of certain tissues can be an indication of disease. Traditional diagnostic methods have relied on the use of manual palpation to discriminate between healthy tissue and diseased regions because imaging methods were unavailable for detecting changes in mechanical properties. For example, the palpation of stiffer tissue is often the first step in the diagnosis of breast cancer and prostate cancer. A change in the mechanical properties of tissue can also be an indicator of the success or failure of therapy.

Elastography is a medical imaging technique that aims to depict elasticity, a mechanical property of tissue. Elasticity is also referred to as stiffness, or the inverse of compliance. Advanced elastography techniques can also measure the viscoelastic properties of tissue, such as viscosity and relaxation time. For this imaging technique, a mechanical excitation is applied in the proximity of the tissue of interest, such as prostate, breast, liver or any other soft organ in the body, and the resulting deformation is measured. The resulting deformation is measured with ultrasound (the method known as ultrasound elastography or USE) or Magnetic Resonance Imaging (the method known as magnetic resonance elastography or MRE). The deformation is post-processed to extract information such as viscoelastic properties (e.g., shear modulus and viscosity). The deformation or tissue strain, or alternatively, the intrinsic mechanical properties of tissue are then displayed as a map of stiffness (or other meaningful mechanical properties) of the imaged object.

Clinical uses of elastography were first demonstrated in the field of ultrasound as described in U.S. Pat. No. 5,107,837 by Ophir et. al. titled "Method and Apparatus for Measurement and Imaging of Tissue Compressibility and Compliance." Shortly afterwards elastography was introduced in the field of magnetic resonance imaging (MRI) by Ehman and Muthupillai as described in U.S. Pat. No. 5,825,186 titled "Method for Producing Stiffness-Weighted MR Images" and U.S. Pat. No. 5,977,770 by Ehman titled "MR Imaging of Synchronous Spin Motion and Strain Waves." In the following years elastography was shown to be of clinical value for the detection and staging of hepatic (liver) fibrosis by Sinkus et. al. "Liver fibrosis: non-invasive assessment with MR elastography" in the Journal NMR in Biomedicine 2006, pages 173-179, and Ehman et. al. "Assessment of Hepatic Fibrosis With Magnetic Resonance Elastography" in the Journal of Clinical Gastroenterology and Hepatology, volume 5, Issue 10, October 2007, pages 1207-1213. Elastography imaging of the breast has been successfully demonstrated and published by Sinkus et. al. in "Viscoelastic shear properties of in vivo breast lesions measured by MR elastography" in the Journal of Magnetic Resonance Imaging volume 23, 2005, pages 159-165. Elastography of the brain was also published by Papazoglou and Braun et. al. in "Three-dimensional analysis of shear wave propagation observed by in vivo magnetic resonance elastography of the brain" in Acta Biomaterialia, volume 3, 2007, pages 127-137. More recently, elastography of the lung was demonstrated by Ehman et. al. In U.S. Pat. No. 2006/0264736 titled "Imaging Elastic Properties of the Lung with Magnetic Resonance Elastography". MRE of the prostate ex-vivo was demonstrated first by Dresner, Rossman and Ehman, published in the Proceedings of the International Society for Magnetic Resonance in Medicine titled "MR Elastography of the Prostate" in 1999. MRE of the prostate in-vivo was demonstrated by Sinkus et. al. and published in "In-Vivo Prostate Elastography", Proceedings of International Society of Magnetic Resonance in Medicine, volume 11, page 586, 2003. Prostate elastography was described in U.S. Pat. No. 5,952,828, 2010/0005892, U.S. Pat. No. 7,034,534 and the publications referred to above and also by Kemper, Sinkus et. al. "MR Elastography of the Prostate: Initial In-vivo Application." published in Fortschritte auf dem Gebiete der Rontgenstrahlen und der Nuklearmedizin (Advances in the area of X-ray and Nuclear Medicine), volume 176, pages 1094-1099, 2004. An alternative approach to prostate elastography used excitation applied through the rectum or the urethra as described in U.S. Pat. No. and 2009/0209847, 2010/0045289 and the following publication Plewes et. al. "In Vivo MR Elastography of the Prostate Gland Using a Transurethral Actuator" Magnetic Resonance in Medicine, volume 62, 2009, pages 665-671. Alternatively, the mechanical excitation can be applied by a needle that penetrates the skin as described in U.S. Pat. No. 2008/0255444.

Quantitative elastography is an advanced elastography technique that solves an inverse problem: calculating the stiffness maps in a region of interest given excitation of the tissue and measurement of resulting motion in that region. Inverse problems are better solved over a 3D (volumetric) than a 2D (cross-sectional planar) region of interest, for example with 3D MRI and 3D ultrasound. This is because knowledge of the tissue motion over a 3D region of interest allows a more complete tissue motion model (e.g. 3D wave equation) to be used. Waves can propagate in arbitrary directions so an inverse algorithm should have 3D data in order to properly compute the wave speed, or spatial wavelength, from which the shear modulus is derived.

It should be clear that the mechanical waves induced by external exciters in most of the previous mentioned techniques vary in both space and time. An ideal measurement system would measure all three components (x,y,z) of the displacements instantaneously over a volume of interest, such that a 3D vector field of 3D displacements can be obtained at many instances in time. Such measurements would form a mathematically complete representation of the wave propagation. However, such ideal measurements systems are currently infeasible, so most previous mentioned works exploit the steady state nature of the wave propagation to build up a representation through multiple measurements over several periods of the waves. This is achieved usually by synchronizing acquisition with the exciter that is creating the waves and assuming perfect periodicity in the excitations. MR imaging is a relatively slow imaging modality, so MR elastography typically requires many minutes of acquisition time. The main advantage is that MR elastography creates high quality quantitative images of the mechanical properties of tissue that are considered the gold standard in the field of elastography. Ultrasound holds promise for faster acquisition yet it poses other challenges to overcome due to the pulse-echo nature of data acquisition and need for multiple pulses, which introduce time delays from both time of flight of the pulses and the delays between pulses. More challenges arise from the desire to acquire data over a 3D volume of interest when using a conventional ultrasound transducer that acquires data from a single 2D cross-sectional plane for a given position of the transducer. It is possible to move a conventional ultrasound transducer over a volume of interest in a freehand fashion, but the set of pulse-echo data will not in general be at equally spaced spatial and temporal locations. This makes it more challenging to use conventional inversion methods to calculate the mechanical properties of tissue from the acquired measurements. There exist methods to interpolate irregularly spaced pulse-echo data of stationary tissue into a regularly spaced volume (see Rohling et al. "Comparison of freehand three-dimensional ultrasound reconstruction techniques" in Medical Image Analysis, 1999), but there are no previous reports of also accommodating the time delays for each pulse-echo step when measuring the displacements of moving tissue. It would be beneficial to invent a method that produces the high quality results of MR elastography with a freehand motion of a conventional ultrasound transducer over a volume of interest, despite the irregular spacing of ultrasound compared to MRI.

Tissue motion, as captured by an ultrasound transducer, usually represents the motion in the axial direction with respect to the ultrasound transducer. The axial direction is defined as the direction of the sound pulse created by the transducer array. The lateral direction is defined in a 2D cross-sectional plane as along the direction of the transducer array, while the elevational direction is defined as orthogonal to the 2D cross-sectional plane. The resolution of an ultrasound image is generally highest in the axial direction and lowest in the elevational direction, so tissue motion in the axial direction is measured with the highest accuracy.

In the U.S. Pat. Application No 2012/000779, by A. Baghani et al., "Elastography using ultrasound imaging of a thin volume", the entirety of which is hereby incorporated by reference, a method is presented to acquire volumetric quantitative elastography images using either matrix arrays that can electronically steer a planar beam to form a 3D volume, such as the xMATRIX ultrasound transducer (Philips Healthcare, Andover, Mass.), or using mechanically swept linear ultrasound imaging transducers, such as the 4DL14-5/38 Linear 4D ultrasound transducer (Ultrasonix Medical Corporation, Richmond, BC), that move the imaging plane in the elevational direction in order to acquire a volumetric image. In the U.S. Pat. Application No 2012/000779, the sweeping motion of the mechanically swept ultrasound transducers is synchronized with the known frequency of the tissue motion in order to generate a set of tissue displacement estimates that are regularly spaced in time and space. As described in the U.S. Pat. Application No. 2012/000779, these displacement estimates can be used to compute elasticity images using techniques known in the art, such as the local spatial frequency estimator.

However, the majority of transducers used with commercial ultrasound machines create only 2D images, so it would be beneficial to extend the benefits of solutions of 3D inverse problems to machines that acquire 2D images.

A standard 2D ultrasound machine can be used to acquire 3D measurements by adding a position tracker to the transducer and then moving the transducer over a 3D region or volume of interest while acquiring ultrasound images—each tagged with one or more position tracker measurements. We assume that the position tracker provides both position and orientation and we will call the joint set of positions and orientations a "location", as commonly done in the robotics literature. A minimum of six numbers is needed to specify the location of an object in space. In this way, the ultrasound image data is acquired at different temporal and spatial locations. This set of ultrasound data is 3D and can be conceptualized by the analogy to stacking a deck of cards, where each card is a 2D ultrasound image. However, since the ultrasound transducer is moved by hand, the set of images will lie on irregularly spaced parallel cross-sections. What is needed is a novel method and system to use the set of tracked ultrasound data in an inverse technique to obtain quantitative elastography.

Previous work such as that performed by Lindop et al ("3D elastography using freehand ultrasound," Ultrasound in Medicine and Biology, 32(4), 2006) demonstrates the ability to create 3D strain volumes using a freehand scanning technique. Unlike the method described in this invention that solves an inverse problem to produce quantitative elastography images, Lindop et al, have created a method using only axial strain imaging. A 2D ultrasound transducer is tracked in 3D space using an active optical tracker. As the transducer is moved, a series of cross-sectional planes are acquired. Each plane is spaced approximately 0.1 mm from its neighbors. They assume that the de-correlation between cross-sectional planes is small and that the small changes in pressure due to the user's motion will cause enough strain to create an elastogram. The strains are calculated using cross-correlation techniques to track the tissue deformation in the axial direction using the radio frequency ultrasound data. However, the Lindop et al method does not provide the quantitative mechanical properties of tissue, but instead, provides the relative strain. The image quality provided with that method can also be compromised by the accumulation of de-correlation due to involuntary motion of the user in all five degrees of freedom that violate the assumptions of only axial compression of tissue. Considerable correction techniques should be applied after the original cross-correlation in order to create an interpretable image. It is also only capable of measuring the static mechanical properties, not the dynamic properties that require measurements over time. Such dynamic techniques are typically based on observing wave motion in tissue.

It is often the case that the frequency of tissue motion exceeds the imaging speed of commercially available ultrasound machines. Vibration frequencies can range from 10 to 300 Hz, while most commercial ultrasound machines produce images at approximately 40 Hz, depending on the depth of imaging. In order to overcome this drawback, two main methods have been developed. The first method uses techniques to speed up the effective frame rate. These techniques could include sector based imaging as described by Baghani et al ("A high-frame-rate ultrasound system for the study of tissue motions", IEEE Ultrasonics, Ferroelectrics and Frequency Control. 57(7), 1535-1547 (2010)).

Another technique involves careful selection of imaging frame rates and vibration frequencies and is described by Eskandari et al ("Bandpass sampling of high frequency tissue motion", IEEE Transactions on Ultrasonics, Ferroelectrics and Frequency Control, 58(7), 2011).

A key application of elastography is surgery where elastograms can guide surgery. The prevalence of minimally invasive surgery, where a surgeon could find benefit from elastogram guidance, is growing. This type of surgery involves the surgeon using long instruments through small holes in the patient's skins. The difficulty of using these instruments to complete complicated procedures led to the development of robotic laparoscopic surgery. In particular, Intuitive Surgical Inc. has commercialized the da Vinci Surgical system. This surgical robot gives the surgeon 6 degrees of freedom of the position and orientation of the end effecter of the tool. This system incorporates a stereo laparoscope, allowing the surgeon to view the surgical scene in 3D. Some embodiments of the invention take advantage of both the dexterity and stereo vision systems of this robot to move and track an ultrasound transducer.

The invention disclosed herein uses a steady-state or periodic excitation to create dynamic motion within a tissue. A tracked 2D ultrasound transducer is used to image the volumetric tissue displacements to create a volume of the mechanical properties of the tissue in real-time without disrupting the natural motion of scanning used by the physician. Tracking of the ultrasound transducer can be achieved, for example, by embedding a magnetic sensor inside the transducer. Note that the scanning motion is described here as arising from the physician's hand, but it could also arise from a robot, where the robot is either moved automatically or controlled by a human operator.

BRIEF DESCRIPTION OF THE INVENTION

According to one aspect of the invention, there is provided a system for imaging the mechanical properties of tissue. The system comprises:
  a) A 2D ultrasound transducer with a linear or curvilinear ultrasound array;
  b) A tracker to measure the position and orientation of the ultrasound transducer;
  c) A mechanical exciter to induce waves in the tissue;
  d) Electronic circuits with inputs of ultrasound echo data and their corresponding 3D position tracker measurements, and outputs for the mechanical exciter, and for the ultrasound transducer pulse transmits;
  e) Software programs that control the mechanical exciter and ultrasound transmits, calculate the delays between exciter and ultrasound echo data, and calculate one or more mechanical properties of the tissue based on the set of ultrasound echo data and 3D position tracker measurements;
  f) Monitor to display to the operator the calculated mechanical properties of tissue over the region of interest.

The ultrasound transducer in this system is non-specific and the system is designed in such a way that any type of ultrasound transducer can be used. In some embodiments of the invention, the ultrasound transducer could have a linear ultrasound transducer array. In some embodiments of the invention, the ultrasound transducer could have a curvilinear ultrasound transducer array. In yet another embodiment, the ultrasound transducer can have a matrix transducer array, exemplified by the xMatrix. For all types of ultrasound transducers, the geometry of the transducer array is known from the manufacturer's specifications and remains constant. This geometry is needed to calculate the spatial location of each pulse-echo beam that is produced relative to each other and the tracker coordinate frame.

We will describe the invention using the embodiment with a transducer having a linear array transducer for the purpose of clarity but not limiting the invention to this particular type of transducer.

The transducer will be tracked through 3D space. This system can be used with multiple types of tracking systems. In some embodiments an electromagnetic ('EM') tracker known in the art, such as those manufactured by Ascension Technology Corporation can be used, in which case the EM sensor is permanently or semi-permanently attached to the ultrasound transducer. In other embodiments of the invention, tracking could be performed using optical tracking, with active markers, as exemplified by the Certus optical tracking system (Northern Digital Instruments), or passive markers, as exemplified by the MicronTracker (Claron Technology Inc.), or by using feature tracking in stereo or mono camera images, through known techniques in the field of image processing, or using robotic kinematics when the transducer is manipulated by a robot. Through calibration techniques (Mercier, et al., "A review of calibration techniques for freehand 3-D ultrasound systems", Ultrasound in Medicine & Biology 31(2), 143-165 (2005)) the position and orientation of the sensor can be related to the position and orientation of the ultrasound imaging crystals and thus an ultrasound image can be recorded at a measured location (position and orientation) in 3D space.

The mechanical exciter should produce vibrations up to a few hundred hertz to measure the elasticity of organs such as the liver, the kidney, and the prostate. For stiffer or smaller organs such as the skin, the frequency of actuation may be higher, up to a couple of kilohertz. The mechanical exciter can be a voice coil actuator as used in speakers or disk drives; it could also be a piezo actuator for higher frequencies; it could also be a conventional motor with an asymmetrical inertial load that may generate vibrations in the same way a cell phone vibrator does. The amplitude and frequency can be controlled through computer software. In some embodiments of the invention, the vibration source can be placed on the patient's skin near the area or organ of interest, whereas in other embodiments of the inventions, the vibration source can be placed inside the patient, directly on the area or organ of interest.

The vibration source will create steady-state dynamic waves in the tissue. Using previously described techniques for high speed/high frame rate ultrasound imaging of tissue motion, the axial displacements of the tissue are tracked. Since the transducer is moving during the data acquisition process, the imaging transmit sequence is synchronized to the excitation such that the tissue displacements will be tracked in 3D space and the temporal delays will be calculated and compensated for in order to create a volumetric dataset of the tissue displacements over specific instances in time. From this dataset, the mechanical properties of the tissue, such as elasticity and viscosity are calculated.

Tissue displacements may be converted from the coordinate system of a tracked ultrasound transducer to a base coordinate system. Converting the displacements from the coordinate system of the tracked ultrasound transducer to the base coordinate system may comprise applying phase compensation for time of flight of ultrasound pulses. Converting the displacements from the coordinate system of the tracked ultrasound transducer to the base coordinate system may comprise applying phase compensation for time delays between subsequent ultrasound pulses.

In addition to the measured tissue displacement, a lack of coherent motion can also give insight into the tissue makeup. Because water and low viscosity fluids like blood do not support shear waves (the type of waves that are causing tissue displacement) the lack of coherent motion is also an indicator to the tissue structure. Structures like vessels can therefore be identified inside organs such as the liver and kidney, and cystic lesions can be differentiated from solid tumours.

In summary, the invention has the following aspects:

A method to measure the mechanical properties of a volume of tissue, the method comprising applying an excitation to the volume of tissue using a vibration source, scanning the volume with a tracked ultrasound transducer, measuring the location of the tracked ultrasound transducer, measuring tissue displacements with respect to the ultrasound transducer from the radiofrequency (RF) transducer echo data, converting these measured displacements to a base coordinate system, and calculating mechanical properties of tissue from the volumetric set of displacements in the base coordinate system.

In some embodiments of the invention, methods of interpolating non-uniform displacement measurements in space are used to create a volumetric datasets of tissue displacements that are uniformly spaced with respect to a base coordinate system.

In some embodiments of the invention, the excitation generated by the vibration source is steady-state.

In some embodiments of the invention, a variety of tracking systems could be used to measure the location of the tracked ultrasound transducer. These tracking systems include but are not limited to, a passive or active optical tracking system, an electromagnetic tracking system or robot kinematics.

In various embodiments of the invention, the vibration source can be placed either on the patient's skin or internally in the patient on the surface of the organ to be imaged.

In various embodiments of the invention, the ultrasound transducer could either be placed on the patient's skin or placed inside the patient and directly adjacent to the area or organ of interest.

In various embodiments of the invention, the coherence of the tissue displacements with respect to a displacement reference such as the vibration source, the motion of a tissue feature or the spatial average motion of a tissue region is computed and used to determine whether the tissue at a specific location is a fluid, such as a blood vessel or a fluid-filled cyst.

In another embodiment of the invention, the reconstruction of the volumetric dataset includes phase compensation for the time of flight of ultrasound pulses.

In another embodiment of the invention, the reconstruction of the volumetric dataset includes phase compensation for the time delays between subsequent ultrasound pulses.

In another embodiment of the invention, the tracked 2D ultrasound transducer moves in a discrete stepwise fashion wherein each step consists of holding the transducer stationary while acquiring tissue displacements from a cross-sectional plane of the volume of interest, and then moving the transducer to an adjacent location, and then repeating.

In another embodiment of the invention, the tracked 2D ultrasound transducer moves in a continuous fashion wherein the transducer is moved without stopping over the volume of interest.

The calculated quantitative mechanical property described in the invention is one of, but not limited to, one of the following: the shear modulus of the tissue, the elasticity of the tissue, the shear wave speed of the tissue, or the shear viscosity of the tissue. The mechanical property calculated using this invention can also include the frequency dependency of a mechanical property, such as those listed above.

BRIEF DESCRIPTION OF THE FIGURES

FIG. 7: Shows a surgical scene including one embodiment of the invention.

DETAILED DESCRIPTION OF THE INVENTION

Detailed descriptions of embodiment of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner. The descriptions of the embodiment of the invention will be made in the publication by Caitlin Schneider, Ali Baghani, Robert Rohling, Septimiu E. Salcudean titled "Remote Ultrasound Palpation for Robotic Interventions using Absolute Elastography", presented at the 15$^{th}$ International Conference on Medical Image Computing and Computer Assisted Intervention, Oct. 2, 2012, Springer LNCS 7510, pp. 42-49, the entirety of which is hereby incorporated by reference.

Figure 1:
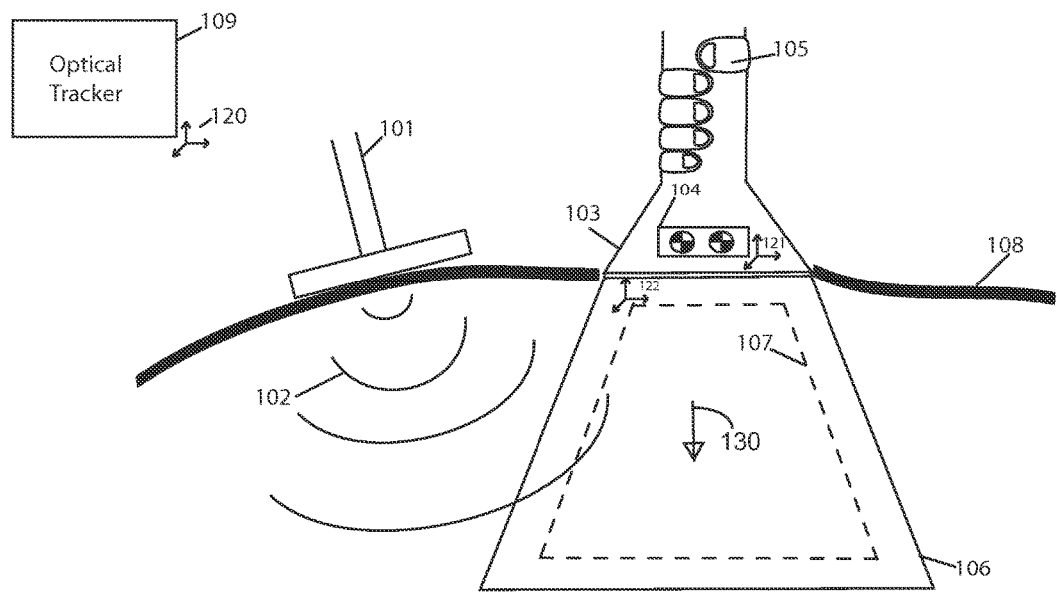
FIG. 1: Set-up of embodiment using an external transducer and excitation.

FIG. 1 shows one embodiment of the invention. In this embodiment, the ultrasound transducer 103 is being held by the user 105 against the patient's skin 108. An external exciter 101 is used as a vibration source for elastography imaging. The waves 102 created by the external exciter 101, propagate through the tissue. The tissue motion caused by these waves 102 is imaged by the ultrasound transducer 103 within the region of interest 107 of the ultrasound image 106. The region of interest 107 will also be called the volume of interest to stress that we are interested in imaging over a volume. As described in the references enclosed therein and known in the state of the art, these motions are measured by repeated capturing of ultrasound pulse-echo data and computing localized delays between such repeated echo data sets using a variety of techniques such as cross-correlation maximization.

The ultrasound transducer 103 in this embodiment is tracked using an optical tracker 109. The optical tracker can be either a passive tracker, using distinctively shaped markers 104 attached to the ultrasound transducer 103. These markers are detected using computer vision techniques. In some embodiments, the markers could be active markers. Active markers emit some type of signal such as coded infrared light pulses that are detected by the optical tracker base station 109.

The transformation between the optical marker 104 and the ultrasound image 106 can be calibrated using techniques such as those described in Mercier et. al ("A review of calibration techniques for freehand 3-D ultrasound systems", Ultrasound in Medicine & Biology 31(2), 143-165 (2005)) giving a single transformation ($T_p$) from the marker coordinate frame 121 to the image coordinate frame 122. The time delay between measurements of the marker position and ultrasound data acquisition, including any lag in either the tracker or ultrasound system, can also be calibrated by one of the techniques described in Mercier et. al. The markers 104 define the ultrasound transducer's 103 position in space with respect to the coordinate frame 120 of the optical tracker base station 109 as a transformation ($T_{ot}$). Thus the position of the ultrasound image 106 and any feature within it can be located in space using a chain of transformations ($T_{ot}$)*($T_p$), determining the image position with respect to the optical tracker 109.

Figure 2:
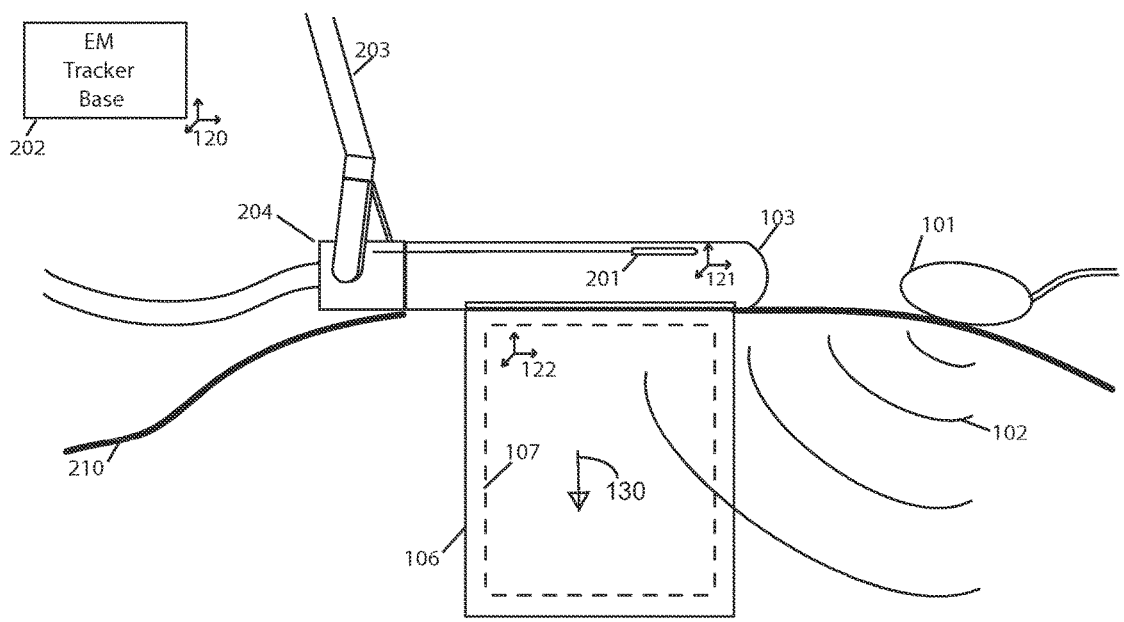
FIG. 2: Embodiment using an intra-operative transducer and internal excitation.

FIG. 2 shows another possible embodiment of the invention. In this embodiment of the invention the ultrasound transducer 103 is a modified laparoscopic transducer, described in detail in C. Schneider et al, ("Intra-operative "Pick-Up" Ultrasound for Robot Assisted Surgery with Vessel Extraction and Registration: A Feasibility Study", IPCAI 2011, and U.S. patent application Ser. No. 13/525,183). This transducer 103 is designed to be used inside the patient's body and placed directly onto the organ or tissue of interest 210. In this embodiment of the invention, the transducer 103 can be picked up and manoeuvred by a robotic tool 203 controlled by the surgeon. The tool 203 picks up the ultrasound transducer 103 by a specially designed tool/transducer interface 204. The control of the ultrasound transducer 103 by the surgeon can either be direct or through tele-operation. In this embodiment, an internal exciter 101 is used to create waves 102 in the tissue. The exciter 101 is placed on or near the organ of interest 210 while ultrasound scans are taking place.

In the embodiment demonstrated by FIG. 2, tracking with respect to a base coordinate system can be completed using an electromagnetic (EM) tracking system, as described in C. Schneider et al, ("Intra-operative "Pick-Up" Ultrasound for Robot Assisted Surgery with Vessel Extraction and Registration: A Feasibility Study", IPCAI 2011 and U.S. patent application Ser. No. 13/525,183). With this type of tracking, an EM sensor 201 is embedded inside the ultrasound transducer 103. The EM Tracker base 202 is placed outside the patient's body and the position of the ultrasound transducer 103 with respect to the EM transmitter 202 can be measured. Tracking takes place similar to the method described above, where the position of the transducer 103 can be found through the combinations of the transformations between coordinate system 120 of the EM Tracker base 202 (the base coordinate system) and the coordinate system 121 of the sensor 201 and the transformation between the sensor coordinate system 121 and the coordinate system of the ultrasound image 122.

By placing the ultrasound transducer 103, the exciter 101 and the organ of interest 210 close together, higher mechanical excitation frequencies can be achieved, because energy dissipation of the waves is less of an issue.

Figure 3:
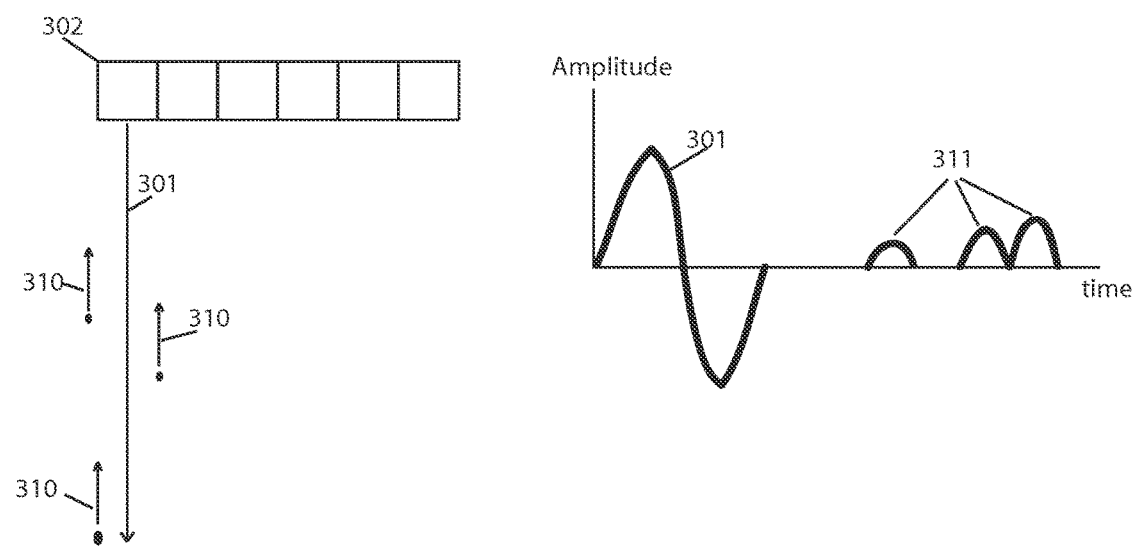
FIG. 3: Description of ultrasound imaging.

FIG. 3 describes the general principle of conventional ultrasound imaging. A sound pulse 301 is emitted from the piezoelectric crystals 302 that make up part of the ultrasound transducer. The sound energy 301 creates reflections 310 where it comes in contact with changes in acoustic impedance. These reflections 310 reflect back to the crystals 302, causing an electric 'echo' 311 to be emitted from the crystal 302. The time delays between the original pulse of sound 301 and receiving the echo 311 define the depth of the change in acoustic impedance.

Changes in the delays in these electrical echoes 311 from tissue motion between repeated imaging sound pulses 301 are measured by delay estimation techniques that are well known in the art, such as cross-correlation. This tissue motion is referred to as the axial motion since it is measured in the axial direction of the transducer 103.

Figure 4:
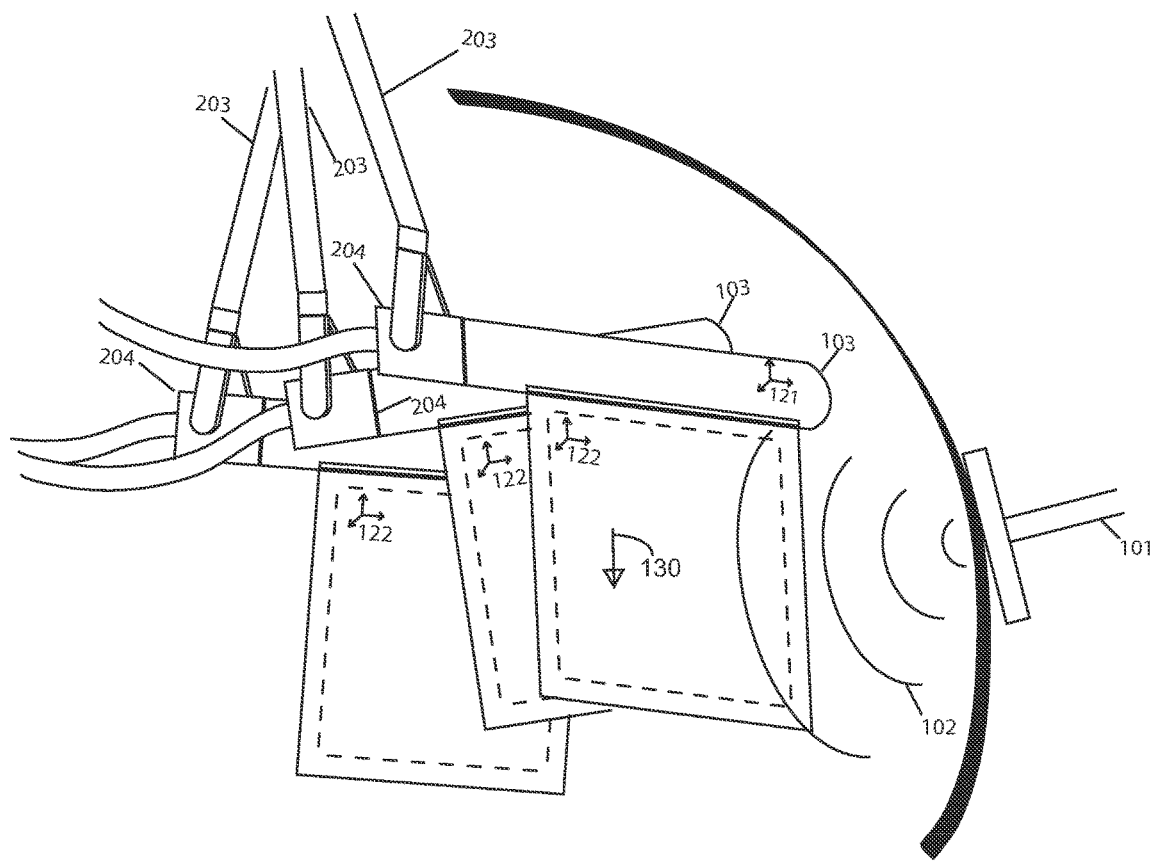
FIG. 4: Set-up of the intra-operative ultrasound transducer in motion.

FIG. 4 shows a method for imaging while the transducer 103 is in motion. The transducer 103 can move with up to 6 degrees of freedom when manipulated by a robotic tool 203. The ultrasound images 106 must be captured in sequence while the transducer 103 is being moved across the tissue. Once the images are captured, they must be reconstructed (FIG. 5).

In some embodiments of the invention, each ultrasound image 106 is taken when the transducer 103 is held still, such that tissue displacements at one spatial location can be measured over multiple instances of time. For example, in the embodiment described in FIG. 1, the imaging sequence is triggered when the transducer 103 is held in place by the user 105, which may be a robot. In one embodiment shown in FIG. 2, the acquisition of pulse-echo data is triggered while the robot is in the clutched state, i.e. when the tools 203 are disengaged from the surgeon control, and therefore the transducer 103 is stationary during the pulse-echo data acquisition. In both cases, capturing while in motion, or stationary, the imaging data needs to be reconstructed into a 3D volume for the most accurate elastogram creation.

Figure 5:
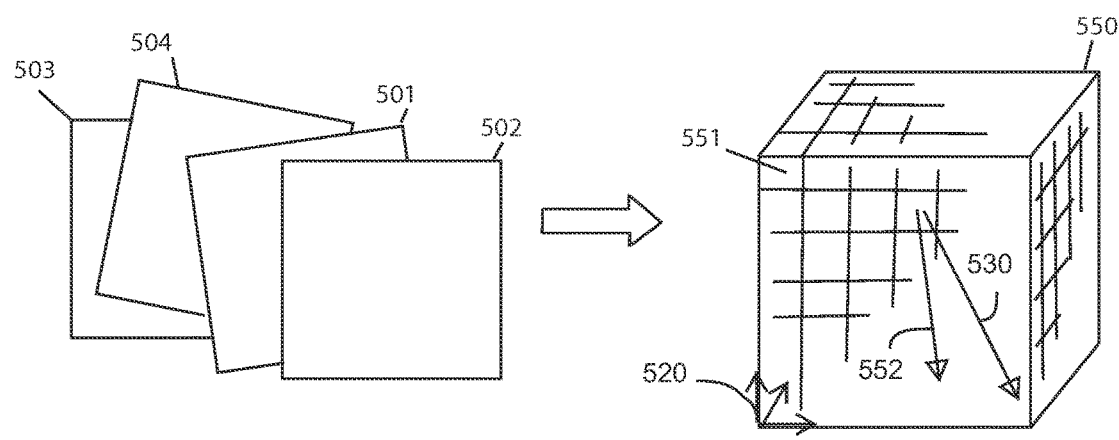
FIG. 5: Shows the reconstruction of multiple ultrasound data acquisition planes into a 3D volume.

FIG. 5 shows how several individual 2D ultrasound images, collected in any of the manners described above, can be used to create a volume of displacements. The captured ultrasound image planes 501-504 are used to create a volume of data 550 by techniques known in the art. In the embodiments of the invention, a thin volume can be created from a few images (5-10), or several seconds of scanning can produce a volume consisting of 50-100 slices. The size of the volume 550 can be determined by the user either before the scan begins, or by terminating the scan. The planes 501-504 can be interpolated into a regularly-spaced volume of data using any of the methods described by Rohling et al ("Comparison of freehand three-dimensional ultrasound reconstruction techniques." Medical Image Analysis, 1999). The techniques described by Rohling et al. can be extended by one skilled in the art from a scalar intensity data to vector displacement data such as that represented in the volume of displacements 550. This can be achieved, for example, by interpolating each of the scalar components of the measured displacement vectors onto the regular grid illustrated in FIG. 5. Thus, at every voxel center 551, there is an associated displacement vector 552, which is obtained from the vectors of displacements 130 in the ultrasound transducer coordinate system 121 (FIG. 2), transformed to vectors 530 of the coordinate system 520 of the volume of displacements 550. When the displacement vectors 130 in the ultrasound transducer coordinate system 121 are complex vectors or phasors, then the above vector interpolation approach is repeated for the real part and the imaginary part of the phasor in a similar way. Hence, within the volume 550, the displacement vectors 552 associated with every voxel center 551 represent the amplitude and phase of tissue motion at each voxel 551 within the volume 550. The coordinate system 520 of the volume of tissue being imaged either coincides with the coordinate system 120 of the ultrasound transducer tracker, or is selected to be close to, or centered at, the volume of tissue being imaged. The chosen location does not affect the elasticity calculations, as the coordinate transformation between the volume coordinate system 520 and the ultrasound transducer tracker coordinate system 120 is known within the interpolation software (Rohling et al, Medical Image Analysis, 1999) and controllable by the user. Hence when we refer to the "base coordinate system", we mean either the base of the tracker 120 or an arbitrary but known coordinate system with respect to which the tissue properties are calculated and displayed. FIG. 6 shows how this method could be used to image a vessel 610. The vessel 610 is filled with blood. The shear waves 102 that are imaged with this elastography method do not propagate in fluids. The motion tracking methods that are used fail to correctly measure motion since reflections 310 from within the vessel are not moving in a coherent way. The loss in coherent motion relative to the motion in the surrounding tissue creates a contrast in the final elastography volume. The level of coherence of tissue motion relative to a reference displacement (such as the exciter displacement, or the displacement of a tissue feature such as an edge, or the spatially averaged displacement of a tissue region) can be computed in a rigorous manner by using the coherence function as described in E. Turgay, S.E. Salcudean and R.N. Rohling, ("Identifying Mechanical properties of Tissue by Ultrasound", Ultrasound in Medicine and Biology, 32(2), pp.221-235, 2006), which is herein incorporated by reference. The coherence function can be displayed as an image of intensities between zero and one. A tissue portion could be determined to be incoherent relative to the reference when the image intensity drops below a threshold value. For example, tissue areas in which the coherence is less than 0.5 are likely to be fluid.

Figure 6A:
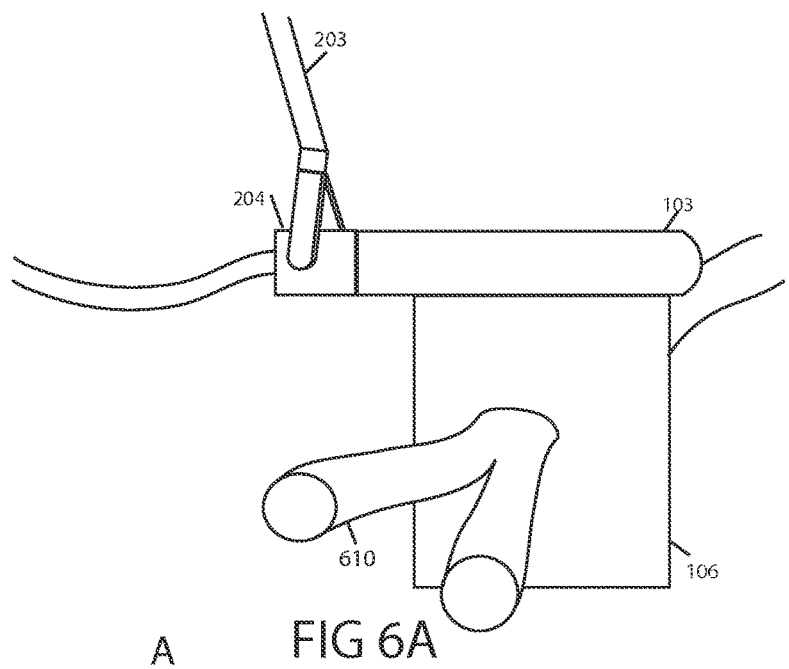
FIGS. 6A, 6B, 6C and 6D: Illustrate how vessels can be imaged with elastography.
Figure 6B:
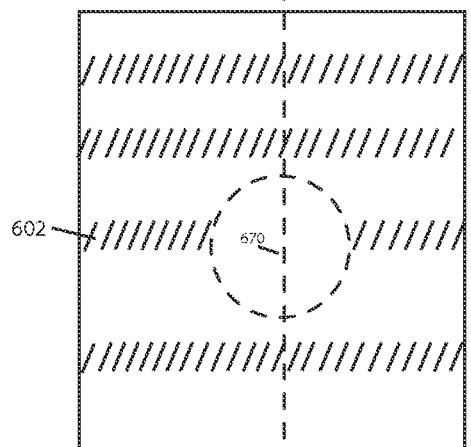

FIG. 6A shows how the transducer 103 would be used in an embodiment as described in FIG. 2. The transducer is held by the robot tool 203 in such a way that the imaging plane 106 intersects with the vessel 610. FIG. 6B shows a wave image 620, where the grey areas 602 represent the wave fronts of the shear waves 102. The area 670 in the center of the wave image 620 represents the cross-section of the vessel 610. The wave fronts 602 are disrupted in this area 670. The amplitude of the waves 102 along the line A are shown in FIG. 6C. The wave pattern within the area 670 is disrupted.

Figure 6D:
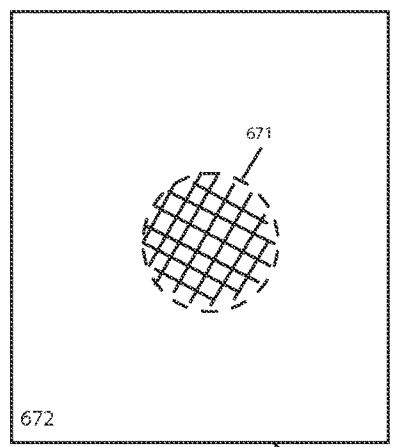
Figure 6C:
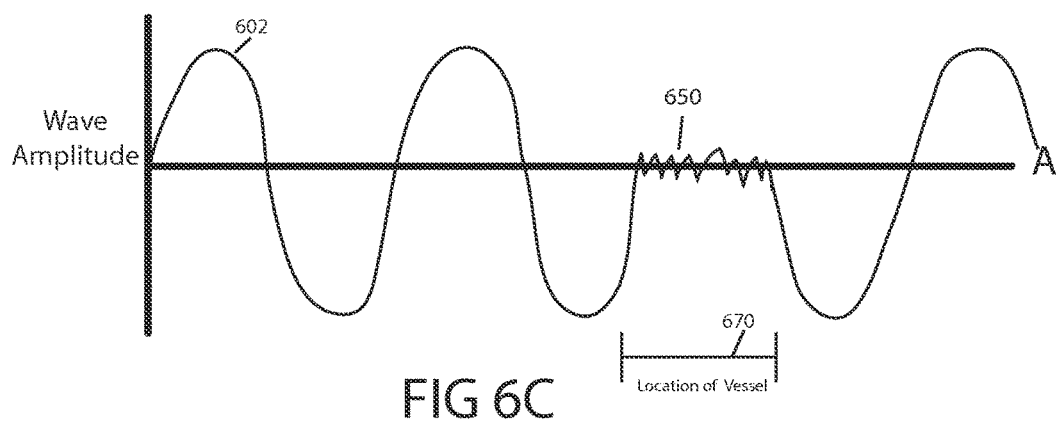

FIG. 6D is a representation of the resulting elastography image 630 using the method described above, where the center area 671 defines the area of the vessel 610. The area 671 of the vessel can be seen in good contrast to the back ground tissue 672.

FIG. 7 shows one embodiment of the invention using the da Vinci laparoscopic robot. The stereo-camera of the da Vinci robot allows the surgical scene to be displayed to the surgeon in 3D dimensions. Using this display, a volume of elasticity 701 can be displayed to the surgeon. The surgical scene displayed in this figure shows the robotic tool 203 manipulating the transducer 103 on the surface of the organ of interest 210, in the embodiment shown, this organ is a kidney, but in other embodiments, the organ of interest could be the prostate, bowel, or other organ. When the scan has been completed and the volume of elasticity 701 can be seen in the place where it was imaged though the stereo display. Within the volume 701, features such as a vessel 720 and a potential tumour 710 are displayed.

Using this method of determining the local elastic properties the loss of the haptic feedback that is typically absent in current robot systems can thus be supplemented by imaging.

Figure 8:
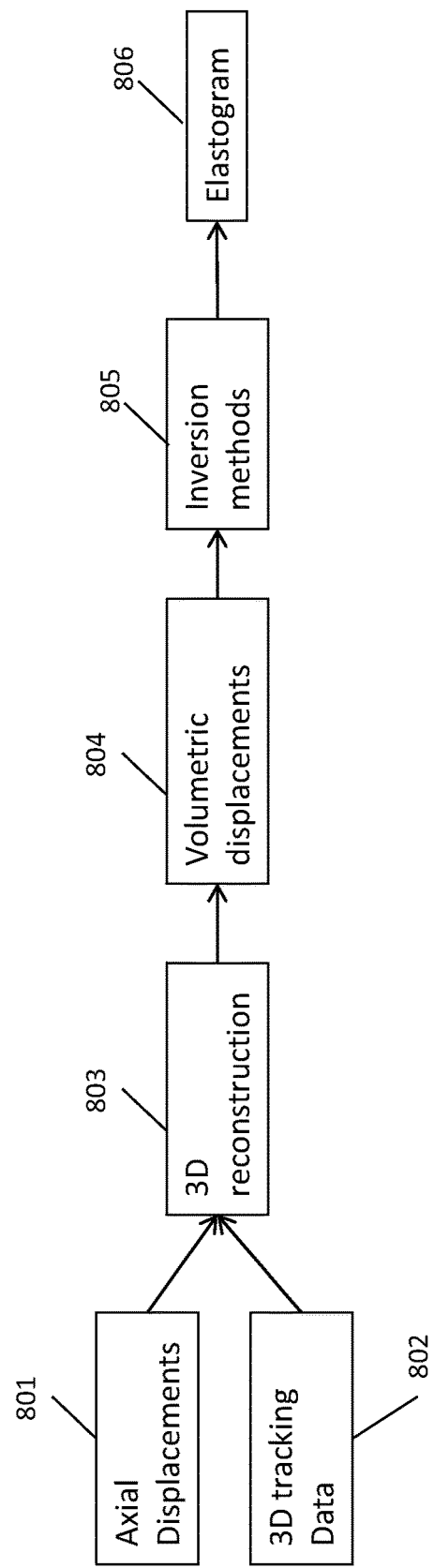
FIG. 8: Describes the overall work flow of the processing in this invention.

FIG. 8 describes one embodiment of the overall workflow of this invention. In this described embodiment, the axial displacements 801 are captured using fast ultrasound imaging techniques (Baghani, A. et al, "A high-frame-rate ultrasound system for the study of tissue motions", IEEE Ultrasonics, Ferroelectrics and Frequency Control. 57(7), 1535-1547 (2010)). The 3D tracking data 802 is combined with the displacements measurements 801 using interpolation methods. The final displacements are reconstructed into a 3D volume 803 to create volumetric displacements 804. Inversion methods 805 such as local frequency estimation (Manduca, A., et al. "Local wavelength estimation for magnetic resonance elastography". IEEE Conference on Image Processing, 1996) are used to determine the spatial wave frequency within the volumetric data. And finally an elastogram 806 is created that represents the elastic properties of the tissue that was imaged. The steps in this embodiment are only one possible from a series of algorithms that could be used. A survey of inversion methods for elastography is presented by Doyley et al ("Model-based elastography: a survey of approaches to the inverse elasticity problem", Physics in Medicine and Biology 57(3), 2012).

What is claimed as the invention is:

1. A method for measuring the mechanical properties in a volume of tissue, the method comprising the steps of:
    applying an excitation to said volume of tissue with a vibration source;
    scanning said volume of tissue with a tracked ultrasound transducer;
    measuring said tracked ultrasound transducer locations relative to a base coordinate system;
    computing tissue displacements relative to said tracked ultrasound transducer from echo data measured by said tracked ultrasound transducer;
    converting said tissue displacements from said tracked ultrasound transducer coordinate system to said base coordinate system using said tracked ultrasound transducer locations; and
    calculating said mechanical properties in said volume of tissue from said tissue displacements in said base coordinate systems;
    wherein said changing of the coordinate system of said tissue displacements to said base coordinate system comprises a phase compensation for time of flight of ultrasound pulses.

2. A method according to claim 1, wherein calculating said mechanical properties comprises interpolating said tissue displacements in said base coordinate system onto a uniform grid.

3. A method according to claim 1, wherein said excitation is steady-state.

4. A method according to claim 1, wherein said tracked ultrasound transducer locations and orientations are measured by a method selected from the group consisting of
    (a) electromagnetic sensing,
    (b) passive or active optical sensing, and
    (c) robot sensing.

5. A method according to claim 1, wherein said vibration source is placed on the skin of a patient.

6. A method according to claim 1, wherein said tracked ultrasound transducer is placed on the skin of a patient.

7. A method according to claim 1, wherein said tracked ultrasound transducer is placed inside a patient and directly adjacent to an area or organ of interest.

8. A method according to claim 1, wherein the calculation of said mechanical properties of tissue comprises calculation of coherence between said tissue displacements and a reference displacement to distinguish soft tissue from a fluid.

9. A method according to claim 1, wherein said tracked ultrasound transducer is moved in a discrete stepwise fashion over said volume of tissue wherein each step comprises holding said tracked ultrasound transducer stationary while measuring said echo data, and then moving said tracked ultrasound transducer to a different location.

10. A method according to claim 1, wherein said tracked ultrasound transducer is moved in a continuous fashion over said volume of tissue.

11. A method according to claim 1, wherein said mechanical properties comprise a quantitative measure of the shear modulus of tissue.

12. A method according to claim 1, wherein said mechanical properties comprise a quantitative measure of the elasticity of the tissue.

13. A method according to claim 1, wherein mechanical properties comprise a quantitative measure of the shear wave speed of the tissue.

14. A method according to claim 1, wherein said mechanical properties comprise a quantitative measure of the shear viscosity of the tissue.

15. A method according to claim 1, wherein said mechanical properties are calculated as a function of frequency.

16. A method according to claim 1, wherein said tracked ultrasound transducer is a matrix transducer array that is capable of both 2D cross-sectional imaging and 3D volumetric imaging.

17. A method for measuring the mechanical properties in a volume of tissue, the method comprising the steps of:
  applying an excitation to said volume of tissue with a vibration source;
  scanning said volume of tissue with a tracked ultrasound transducer;
  measuring said tracked ultrasound transducer locations relative to a base coordinate system;
  computing tissue displacements relative to said tracked ultrasound transducer from echo data measured by said tracked ultrasound transducer;
  converting said tissue displacements from said tracked ultrasound transducer coordinate system to said base coordinate system using said tracked ultrasound transducer locations; and
  calculating said mechanical properties in said volume of tissue from said tissue displacements in said base coordinate systems;
wherein said vibration source is placed internally in a patient on the surface of an organ to be imaged.

18. A method for measuring the mechanical properties in a volume of tissue, the method comprising the steps of:
  applying an excitation to said volume of tissue with a vibration source;
  scanning said volume of tissue with a tracked ultrasound transducer;
  measuring said tracked ultrasound transducer locations relative to a base coordinate system;
  computing tissue displacements relative to said tracked ultrasound transducer from echo data measured by said tracked ultrasound transducer;
  converting said tissue displacements from said tracked ultrasound transducer coordinate system to said base coordinate system using said tracked ultrasound transducer locations; and
  calculating said mechanical properties in said volume of tissue from said tissue displacements in said base coordinate systems;
wherein said changing of the coordinate system of said tissue displacements to said base coordinate system comprises a phase compensation for time delays between subsequent ultrasound pulses.

* * * * *